US012810425B2

(12) United States Patent
Jhong et al.

(10) Patent No.: US 12,810,425 B2
(45) Date of Patent: Nov. 24, 2026

(54) SCALP CONDITION CLASSIFICATION SYSTEM AND SCALP CONDITION CLASSIFICATION METHOD

(71) Applicant: MacroHI Co., Ltd., New Taipei City (TW)

(72) Inventors: Sin-Ye Jhong, New Taipei City (TW); Chih-Hsien Hsia, Taipei (TW); Chun-Wei Chen, New Taipei City (TW)

(73) Assignee: MacroHI Co., Ltd., New Taipei City (TW)

( * ) Notice: Subject to any disclaimer, the term of this patent is extended or adjusted under 35 U.S.C. 154(b) by 216 days.

(21) Appl. No.: 18/977,861

(22) Filed: Dec. 11, 2024

(65) Prior Publication Data

US 2026/0112026 A1 Apr. 23, 2026

(30) Foreign Application Priority Data

Oct. 21, 2024 (TW) ................................ 113139961

(51) Int. Cl.
*G06T 7/00* (2017.01)
*G06V 10/42* (2022.01)
(Continued)

(52) U.S. Cl.
CPC ............ *G06T 7/0012* (2013.01); *G06V 10/42* (2022.01); *G06V 10/761* (2022.01);
(Continued)

(58) Field of Classification Search
CPC . G06T 2207/20004; G06T 2207/20081; G06T 2207/30088; G06T 2207/30196;
(Continued)

(56) References Cited

U.S. PATENT DOCUMENTS

2021/0224610 A1* 7/2021 Jha ......................... G06V 10/82
2022/0335614 A1 10/2022 Punyani et al.
2024/0331137 A1 10/2024 Heng et al.

FOREIGN PATENT DOCUMENTS

CN 116304061 A 7/2023
CN 116664585 A 8/2023
(Continued)

OTHER PUBLICATIONS

An Edge-Cloud Collaborative Scalp Inspection System Based on Robust Representation Learning Sin-Ye Jhong, Guan-Ting Li, and Chih-Hsien Hsia, IEEE Transactions on Consumer Electronics Date:Dec. 1, 2024.

(Continued)

*Primary Examiner* — Kenny A Cese
(74) *Attorney, Agent, or Firm* — Bruce Stone LLP; Joseph A. Bruce

(57) ABSTRACT

A scalp condition classification system and method designed to address limitations of traditional data augmentation techniques are provided. Scalp condition classification system includes an image preprocessing module that generates augmented images while preserving all original image features, ensuring that no potential symptoms are removed. An encoder extracts features from the augmented images, which are subsequently augmented through a prototype-based augmentation module that incorporates features corresponding to predefined scalp conditions. The system further includes a positive classifier and a negative classifier, each configured to process the augmented features and output a first set of and a second set of predictions, respectively. A loss calculation module calculates supervised loss using actual labels and computes reverse consistency loss between the prediction results. To adjust the system during the inference process in testing, an adaptive update module minimizes a (Continued)

sharpness-aware and reliable entropy loss, ensuring stable classification performance across diverse imaging devices and environments.

19 Claims, 6 Drawing Sheets

(51) Int. Cl.

| | |
|---|---|
| ***G06V 10/74*** | (2022.01) |
| ***G06V 10/764*** | (2022.01) |
| ***G06V 10/77*** | (2022.01) |
| ***G06V 10/771*** | (2022.01) |
| ***G06V 10/776*** | (2022.01) |
| ***G06V 10/82*** | (2022.01) |
| ***G16H 50/70*** | (2018.01) |

(52) U.S. Cl.

CPC .......... *G06V 10/764* (2022.01); *G06V 10/771* (2022.01); *G06V 10/7715* (2022.01); *G06V 10/776* (2022.01); *G06V 10/82* (2022.01); *G16H 50/70* (2018.01); *G06T 2207/20004* (2013.01); *G06T 2207/20081* (2013.01); *G06T 2207/30088* (2013.01); *G06T 2207/30196* (2013.01); *G06V 2201/03* (2022.01)

(58) Field of Classification Search

CPC ...... G06T 7/0012; G06V 10/42; G06V 10/74; G06V 10/761; G06V 10/764; G06V 10/771; G06V 10/7715; G06V 10/774; G06V 10/776; G06V 10/82; G06V 2201/03; G06V 40/10; G16H 50/70

See application file for complete search history.

(56) References Cited

FOREIGN PATENT DOCUMENTS

| | | | |
|---|---|---|---|
| CN | 117242482 | A | 12/2023 |
| CN | 117407768 | A | 1/2024 |
| TW | 201914524 | A | 4/2019 |

OTHER PUBLICATIONS

Balanced Contrastive Learning for Long-Tailed Visual Recognition Jianggang Zhu, Zheng Wang, Jingjing Chen, Yi-Ping Phoebe Chen, and Yu-Gang Jiang Date: 2022.

ScalpEye: A Deep Learning-Based Scalp Hair Inspection and Diagnosis System for Scalp Health Wan-Jung Chang, Liang-Bi Chen, Ming-Che Chen, Yi-Chan Chiu, and Jian-Yu Lin Date:Jul. 21, 2020.

MutexMatch: Semi-Supervised Learning with Mutex-Based Consistency Regularization Yue Duan, Zhen Zhao, Lei Qi, Lei Wang, Luping Zhou, Yinghuan Shi, Yang Gao / Dec. 21, 2022 / IEEE Transactions on Neural Networks and Learning Systems (TNNLS).

FeatMatch: Feature-Based Augmentation for Semi-Supervised Learning Chia-Wen Kuo, Chih-Yao Ma, Jia-Bin Huang, Zsolt Kira / Jul. 16, 2020 / Feb. 24, 2023 / Paper accepted in ECCV 2020.

Towards Stable Test-Time Adaptation in Dynamic Wild World Shuaicheng Niu, Jiaxiang Wu, Yifan Zhang, Zhiquan Wen, Yaofo Chen, Peilin Zhao, Mingkui Tan / Feb. 24, 2023 / accepted by International Conference on Learning Representations (ICLR) 2023 as Notable-Top-5%; 27 pages, 10 figures, 18 tables.

* cited by examiner

SCALP CONDITION CLASSIFICATION SYSTEM AND SCALP CONDITION CLASSIFICATION METHOD

FIELD OF THE INVENTION

The present invention relates to systems and methods for medical image classification using artificial intelligence (AI), specifically for the classification of scalp conditions. More particularly, the invention pertains to a system and method that utilizes advanced image preprocessing techniques, prototype-based feature augmentation, and adaptive model inference to accurately classify scalp conditions such as folliculitis, seborrheic dermatitis, oily dandruff, psoriasis, dry dandruff, and normal scalp.

BACKGROUND OF THE INVENTION

Classification of scalp conditions is a critical component in dermatological medicine and healthcare. Traditionally, professionals specializing in scalp health have primarily relied on visual examinations and, at times, microscopic analysis of scalp samples to diagnose these conditions. However, these methods can yield subjective, time-consuming, and variable results due to differences in the expertise of the professionals and the quality of the imaging equipment used.

With the advancement of digital imaging and artificial intelligence (AI) technologies, there has been significant progress in developing automated systems to assist in the diagnosis of scalp conditions. These systems typically involve training machine learning models on large, annotated datasets of scalp images to classify various scalp conditions. While these approaches demonstrate considerable potential, several challenges still limit their effectiveness in clinical applications.

One major challenge is the variability in image quality and appearance caused by differences in imaging devices and environmental factors. For instance, images captured under varying lighting conditions, at different resolutions, or using different types of imaging equipment may exhibit substantial differences that can adversely affect the accuracy of AI-based classification systems. Additionally, the diversity of scalp conditions and their manifestations necessitates that models generalize well across different patient populations, a requirement that is difficult to achieve with traditional machine learning techniques.

Another significant challenge is the need for robust data augmentation techniques that can preserve all critical features of scalp images. Conventional augmentation methods, such as cropping, may inadvertently remove portions of the scalp image containing key symptoms, leading to inaccurate classifications. Ensuring that augmentation techniques maintain the integrity of diagnostic features is essential for the development of reliable classification systems.

Therefore, there is a need for an improved system and method for classifying scalp conditions that can provide stable and accurate classifications under varying imaging conditions while retaining the critical diagnostic features present in scalp images.

SUMMARY OF THE INVENTION

The present invention provides a system and method for classifying scalp conditions using scalp images, aimed at overcoming challenges related to variability in imaging conditions and the limitations of traditional data augmentation techniques. By combining prototype-based feature augmentation, positive and negative classifiers, and adaptive models, the invention improves the accuracy and stability of scalp condition classification.

To achieve the above objectives and others, the invention provides a scalp condition classification system that includes an image preprocessing module configured to receive an input scalp image and generate multiple augmented images by applying operations that preserve all original image features, ensuring that no potential symptoms are removed. These operations include, but are not limited to, rotating and swapping portions of the scalp image. These techniques enhance the system's generalization capabilities under varying conditions while maintaining the integrity of the original image content.

The scalp condition classification system further includes an encoder configured to extract features from the augmented images. The extracted features are subsequently processed by a prototype-based augmentation module, which combines prototype features corresponding to predefined scalp conditions. These prototypes are selected based on a similarity measure (such as cosine similarity) between the extracted features and a set of predefined class prototypes. The similarity measure can be enhanced using a temperature-scaled softmax function to improve the accuracy of prototype integration.

The classification module of the scalp condition classification system includes a positive classifier and a negative classifier. The positive classifier is configured to process the augmented features and output a first set of predictions, while the negative classifier processes the augmented features and outputs a second set of predictions. The positive and negative classifiers work collaboratively by focusing on both the affirmative and negating aspects of the image, accurately distinguishing various scalp conditions and thereby enhancing the robustness and precision of classification.

Additionally, the scalp condition classification system includes a loss calculation module configured to compute supervised loss using actual labels and to calculate reverse consistency loss between the first set of predictions and the second set of predictions. This ensures that the scalp condition classification system is trained on professionally annotated data, mitigating the risks associated with the use of pseudo-labels.

To address the issue of variability in imaging conditions caused by different devices and environmental factors, the scalp condition classification system is equipped with an adaptive update module. During inference in testing, the adaptive update module adjusts the system by minimizing a sharpness-aware and reliable entropy loss. The adaptive update module filters out samples that generate large gradient norms, which could destabilize the adaptation process, and ensures convergence to flat minima in loss calculations. This approach enhances the stability and reliability of the AI model in diverse and challenging real-world scenarios.

To achieve the aforementioned objectives and others, the invention also provides a method for classifying scalp conditions. The scalp condition classification method includes receiving an input scalp image, generating multiple augmented images that preserve all original image features, extracting features from the augmented images, and using a prototype-based augmentation module to augment these features. The method further includes processing the augmented features through positive and negative classifiers to output first and second sets of predictions, respectively. The method also involves calculating supervised loss and reverse consistency loss, and adjusting the system during the inference process to ensure stable classification performance.

The invention significantly improves upon existing solutions by preserving critical diagnostic features during data augmentation, using prototype-based augmentation to better differentiate similar scalp conditions, and applying robust adaptive techniques during inference to maintain accuracy under varying imaging environments. The result is a more reliable, adaptable, and precise scalp condition diagnostic system, which is essential in medical applications requiring high levels of accuracy and consistency.

Advantages Over Existing Solutions:

1. Retention of Critical Diagnostic Features: By preserving all original image features during data augmentation, the system ensures that no essential symptoms are lost, which is crucial for accurate diagnosis.
2. Enhanced Differentiation Through Prototype-Based Augmentation: Utilizing prototypes allows the AI model to leverage prior knowledge about scalp conditions, enabling more precise differentiation between similar conditions.
3. Robust Adaptive Techniques for Varied Imaging Environments: The application of sharpness-aware and reliable entropy minimization strategies during inference ensures that the AI model maintains high accuracy and stability across diverse and challenging imaging conditions.

In summary, the present invention not only enhances the diagnostic process by providing automated and accurate classification of scalp conditions but also offers a flexible and scalable solution that can be integrated into various clinical workflows. The combination of advanced feature extraction, prototype-based augmentation, and adaptive inference ensures that the scalp condition classification system can effectively handle the complexities of scalp image classification.

BRIEF DESCRIPTION OF THE DRAWINGS

The objects, spirits, and advantages of the preferred embodiments of the present disclosure will be readily understood by the accompanying drawings and detailed descriptions, wherein.

DESCRIPTION OF THE PREFERRED EMBODIMENTS

The present invention relates to a system and method for accurately classifying scalp conditions using medical imaging. The invention aims to address challenges associated with variability in imaging conditions, limitations of traditional data augmentation techniques, and the need for robust classification models in medical diagnostics. By leveraging advanced image preprocessing techniques, prototype-based feature augmentation, and adaptive model inference, the invention enhances the accuracy, reliability, and robustness of scalp condition classification systems.

Accurately classifying scalp conditions such as folliculitis, seborrheic dermatitis, oily dandruff, psoriasis, dry dandruff, and normal scalp is of significant importance to relevant professionals. Traditional methods typically rely on trained specialists conducting visual inspections or microscopic analyses, which may be subjective and yield inconsistent results. With advancements in digital imaging and artificial intelligence, there is an increasing demand for automated systems that can assist in diagnosing scalp conditions more precisely and consistently.

The present invention is particularly advantageous in clinical environments where imaging conditions may vary due to different equipment, lighting, and environmental factors. By preserving the integrity of the original medical images and employing sophisticated feature augmentation and classification techniques, the invention ensures that all relevant diagnostic information is retained and utilized to achieve accurate classification results.

Figure 1:
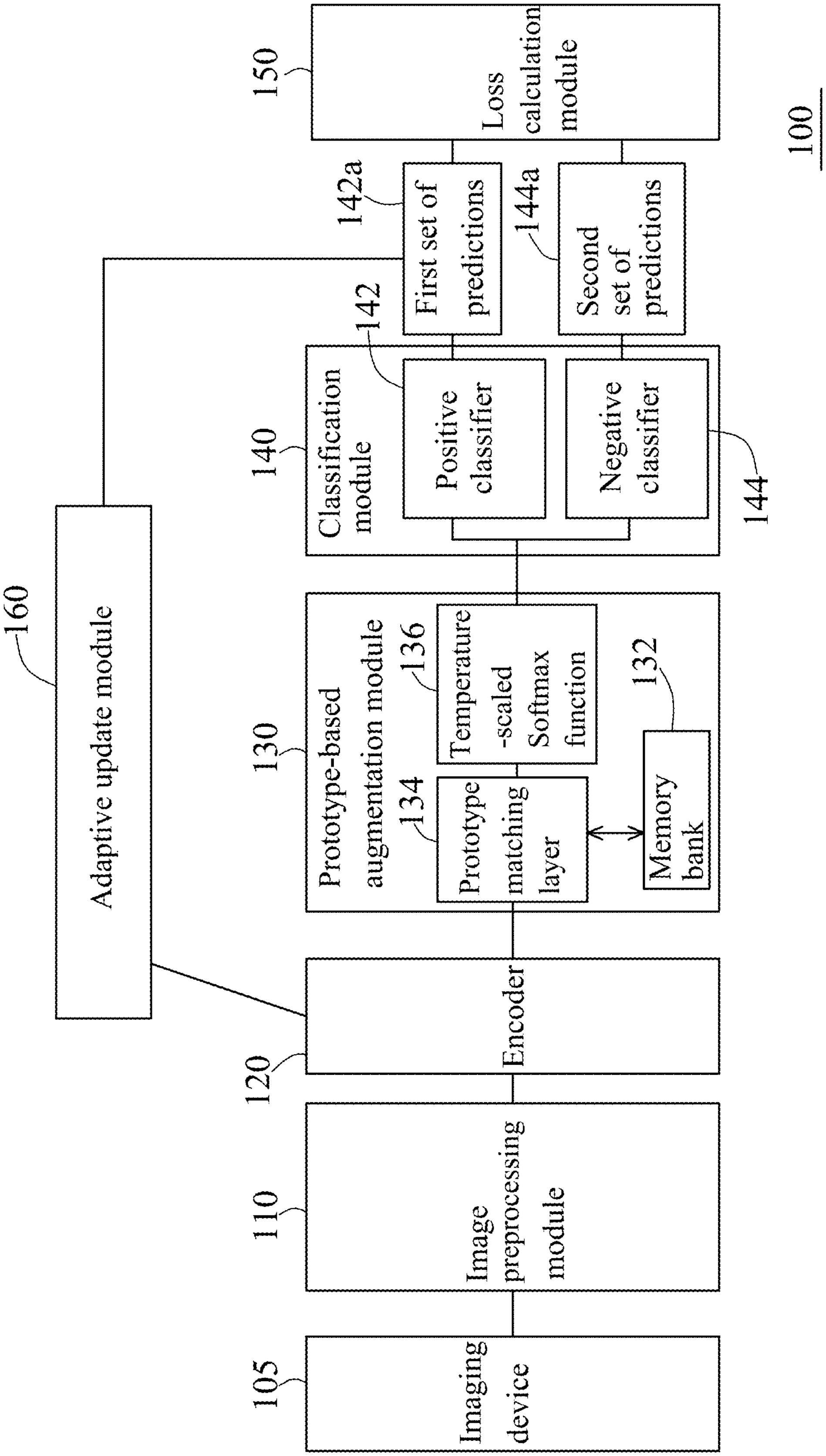
FIG. 1 is a block diagram of an embodiment of the scalp condition classification system according to the present invention.

Referring to FIG. 1, there is illustrated a block diagram of an embodiment of the scalp condition classification system according to the present invention. The scalp condition classification system 100 includes an image preprocessing module 110, an encoder 120, a prototype-based augmentation module 130, a classification module 140 (including a positive classifier 142 and a negative classifier 144), a loss calculation module 150, and an adaptive update module 160. The training process of the scalp condition classification system 100 will be described first.

Figure 2:
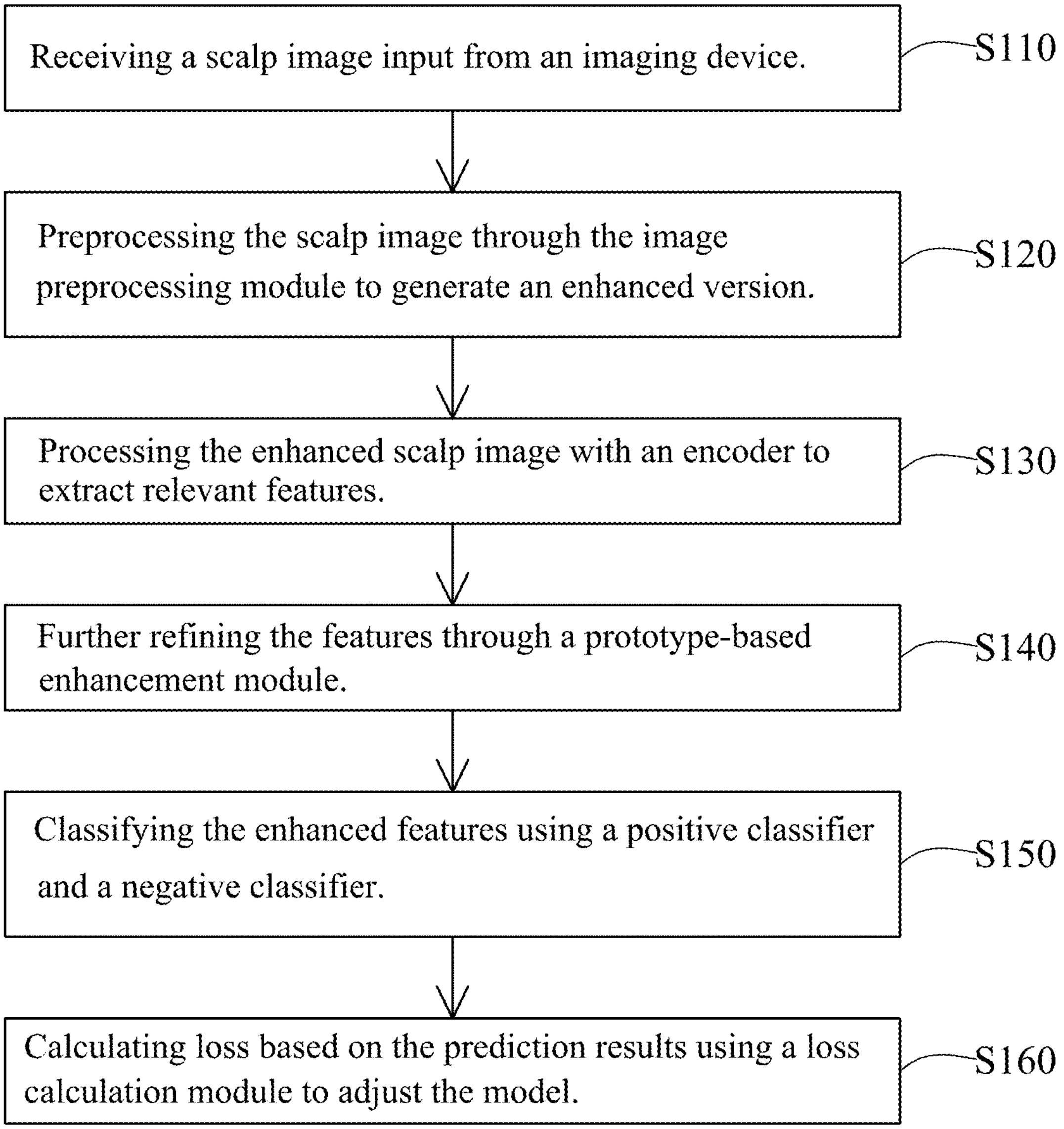
FIG. 2 is a flowchart of an embodiment of the scalp condition classification system according to the present invention.
Figure 3A:
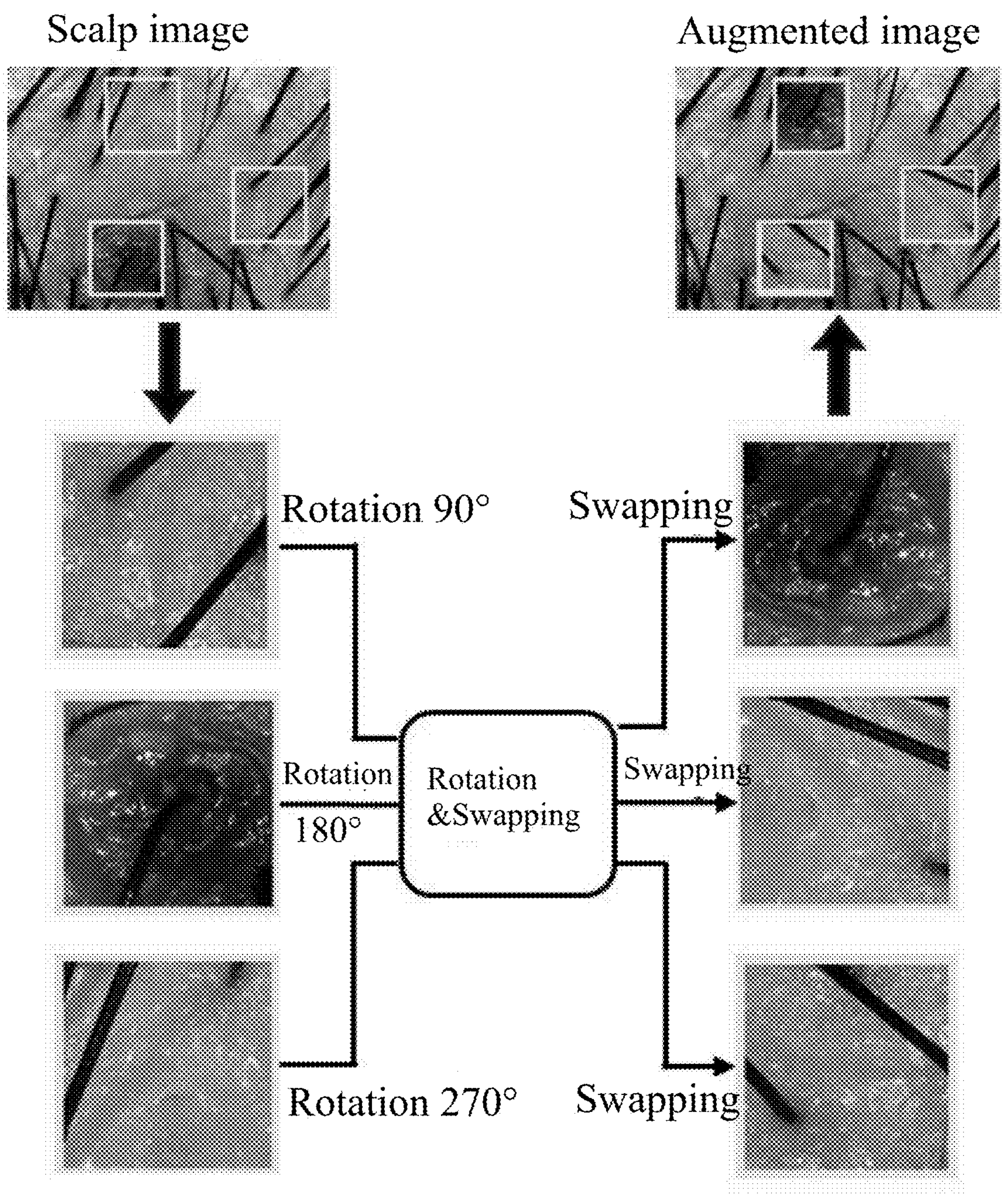
FIG. 3A is a scalp image input by the imaging device of the scalp condition classification system.

Additionally, referring to both FIG. 1 and FIG. 2, FIG. 2 illustrates a flowchart of an embodiment of the scalp condition classification system according to the present invention. First, as shown in step S110, the scalp condition classification system 100 receives scalp image 10 (as shown in FIG. 3A) input from imaging device 105. Next, as shown in step S120, the scalp image 10 is preprocessed by the image preprocessing module 110 to generate at least two augmented versions of the scalp image, 10' and 10". The scalp image 10' retains all features of the original image 10. Subsequently, as shown in step S130, these augmented scalp images 10' and 10" are processed by encoder 120 to extract relevant features. Then, as shown in step S140, these features are further refined by the prototype-based augmentation module 130. Next, as shown in step S150, the augmented features are classified by the positive classifier 142 and the negative classifier 144. Afterwards, as shown in step S160, the loss calculation module 150 of the scalp condition classification system 100 calculates the loss based on the prediction results to adjust the model. After training is completed, the scalp condition classification system 100 uses the adaptive update module 160 during testing or inference to adapt to different imaging conditions, ensuring consistent and accurate classification results in diverse environments. The following provides a more detailed introduction to the aforementioned components and steps.

The image preprocessing module 110 is responsible for preparing the input scalp images for further processing by the scalp condition classification system 100. Considering the critical importance of preserving all diagnostic information in medical images, the image preprocessing module 110 is designed to generate augmented versions of the input scalp image 10, namely scalp images 10' and 10", without removing any features that may indicate scalp conditions.

Figure 3B:
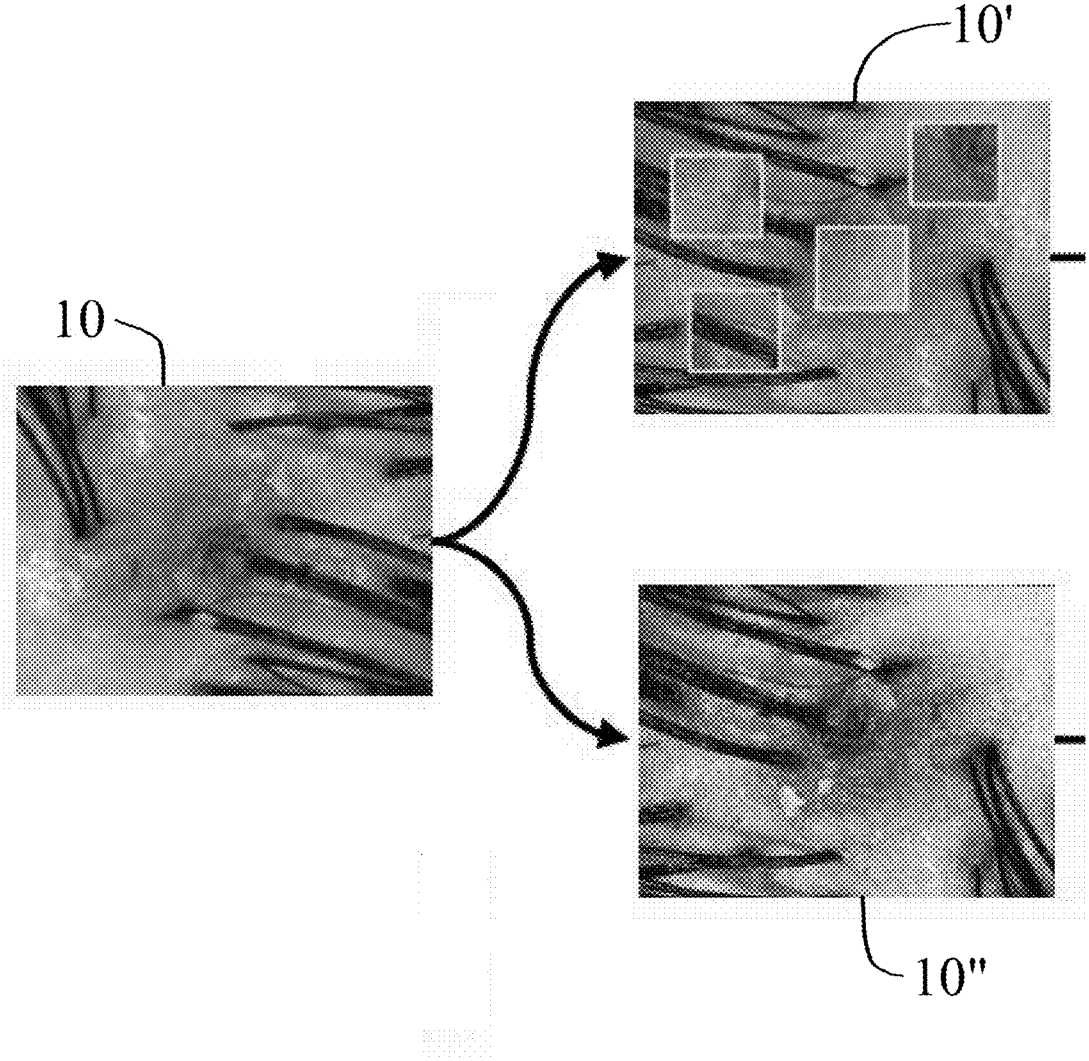
FIG. 3B is a series of operations that the image preprocessing module may employ.

As shown in FIG. 3B, the image preprocessing module 110 may employ a series of operations, including rotation and swapping techniques, to create at least two augmented images, 10' and 10", from the original input scalp image 10 (as shown in FIG. 3A). These operations must ensure that no parts of the image containing symptoms are lost or altered, thereby affecting classification accuracy. For example, the image preprocessing module 110 may use a rotation operation, which includes rotating the input image by predetermined angles (e.g., 90°, 180°, 270°). This technique helps the AI model learn invariant features by exposing it to the same scalp image 10 from different orientations. This is particularly useful in medical-related images, as the direction of symptoms may vary across different images.

In this embodiment, the AI model refers to the portion of the scalp condition classification system 100 that involves neural network architectures and their learning parameters, primarily located within the encoder 120, prototype-based augmentation module 130, and classification module 140. The adaptive update module 160 interacts with the "AI model" by updating parameters during the inference process based on test data.

Additionally, the swapping operation involves exchanging parts of the image without removing any content. This technique breaks the uniformity of the image background while maintaining the integrity of critical features. By doing so, the scalp condition classification system 100 is trained to focus on prominent features indicative of scalp conditions rather than being influenced by irrelevant background patterns.

By applying these operations, the image preprocessing module 110 generates a set of diversified scalp images, namely 10' and 10", enhancing the robustness of subsequent feature extraction and classification stages. The adopted augmentation strategies specifically avoid methods such as cropping, which may remove portions of the scalp image 10 that contain critical diagnostic information.

Referring again to FIG. 1, the encoder 120 is a key component of the scalp condition classification system 100, responsible for extracting meaningful features from the augmented images generated by the image preprocessing module 110. The role of encoder 120 is to transform the input scalp images 10' and 10" into a high-dimensional feature space, where relevant features of scalp conditions can be effectively captured and distinguished.

In this embodiment, the encoder 120 is typically implemented as a convolutional neural network (CNN), designed to handle the spatial hierarchical structures in image data. The CNN may consist of multiple convolutional layers, each followed by a nonlinear activation function (e.g., ReLU), pooling layers, and normalization layers. These layers work collaboratively to progressively abstract the input images into a set of features capturing various levels such as texture, color, shape, and edge information. As the input images pass through the convolutional layers, they are transformed into feature maps that highlight specific patterns and structures within the images. These feature maps are subsequently processed by pooling layers to reduce their dimensionality, retaining the most important information while discarding redundant details. After the final convolutional layer, the output feature maps are flattened into high-dimensional feature vectors. These high-dimensional feature vectors represent the fundamental characteristics of the input scalp images, for further processing by the prototype-based augmentation module 130 and classification module 140 of the scalp condition classification system 100.

The prototype-based augmentation module 130 plays a critical role in refining the features extracted by the encoder 120, enhancing the ability of the scalp condition classification system 100 to accurately classify scalp conditions. This prototype-based augmentation module 130 utilizes predefined class prototypes to augment feature vectors, effectively guiding the learning process of the AI model (i.e., the scalp condition classification system 100) by incorporating prior knowledge about the conditions being classified.

In this embodiment, a "prototype" refers to a representative feature vector that encapsulates the most prominent characteristics of a specific class. Prototypes serve as reference points in the feature space, representing the typical features that define particular scalp conditions. During training, the scalp condition classification system 100 learns to generate feature vectors for each input scalp image. These feature vectors are then grouped based on their corresponding scalp condition labels. By applying clustering techniques, such as K-Means clustering, the scalp condition classification system 100 identifies the most representative feature vectors within each class cluster. These most representative feature vectors are designated as the prototypes for their respective classes. Prototypes act as anchors or reference points to help the scalp condition classification system 100 compare new, unseen feature vectors against established class standards. When the scalp condition classification system 100 encounters a new image, it extracts its feature vector and compares it with stored prototypes using similarity measures (such as cosine similarity). The prototype closest to the new feature vector provides the basis for feature augmentation, thereby enhancing the ability of the scalp condition classification system 100 to correctly classify the scalp image. The use of prototypes enables the scalp condition classification system 100 to better generalize to new samples not seen during training. Since prototypes represent the core features of each class, they help the scalp condition classification system 100 identify and classify new images similar to the prototype examples, even if these specific images differ somewhat from those seen during training.

In this embodiment, prototypes are selected based on a similarity measure (e.g., cosine similarity) between the feature vectors extracted by the encoder 120 and the predefined class prototypes. Cosine similarity evaluates the angle between two vectors in the feature space, providing a robust indicator for assessing the similarity between different feature vectors. In this embodiment, the similarity measurement is performed by the prototype matching layer 134. The prototype matching layer 134 outputs a similarity score for each prototype and then selects the most relevant prototypes for enhancing the input features.

To further refine the prototype selection process, the scalp condition classification system 100 applies a Temperature-Scaled Softmax function 136. This Softmax function 136 adjusts the sharpness of the similarity distribution, allowing the scalp condition classification system 100 to control the confidence level of prototype assignments. By adjusting the temperature parameter of the Softmax function 136, the scalp condition classification system 100 can emphasize the most similar prototypes or more broadly distribute attention across multiple prototypes based on the specific needs of the classification task.

Once the relevant prototypes are selected, they are combined with the original feature vectors (i.e., the feature vectors extracted by the encoder 120) to create augmented feature vectors. This augmentation process involves merging the original features with the selected prototypes to improve the model's ability to distinguish between different scalp conditions. The augmented feature vectors are more discriminative because they not only include the original information from the input images but also incorporate background knowledge provided by the prototypes.

In this embodiment, the prototype-based augmentation module 130 also includes a memory bank 132 for storing the extracted features and their corresponding actual labels during the training process. This memory bank 132 serves as a repository for the feature vectors generated by the encoder 120, allowing the scalp condition classification system 100 to reference historical records of feature representations during prototype updates. During training, the memory bank 132 is periodically updated with new data, which is used to refine the prototype features, ensuring they remain representative of the most current and diverse dataset. This dynamic update mechanism enables the scalp condition classification system 100 to adapt to new information while maintaining the stability of its prototype-based augmentation strategy.

The periodic update of the memory bank 132 is intended to maintain the relevance and accuracy of the prototypes over time. The scalp condition classification system 100 includes a mechanism for updating the prototype features based on regular intervals or newly received scalp images during the training process. As new data is incorporated into the memory bank 132, the prototypes dynamically adjust to reflect the latest trends and variations in the feature space. This update process is critical for ensuring that the prototypes continue to accurately represent all conditions and variabilities present in the recent data. By regularly refining the prototypes, the scalp condition classification system 100 ensures that they remain effective in guiding the feature augmentation process, thereby improving the overall classification accuracy.

Referring again to FIG. 1, the positive classifier 142 of the classification module 140 generates an initial set of predictions based on the augmented feature vectors generated by the prototype-based augmentation module 130. In this embodiment, the positive classifier 142 may consist of one or more fully connected neural network layers that take the augmented feature vectors as input. The positive classifier 142 processes these augmented feature vectors to generate a probability distribution over a predefined set of scalp conditions. Each output value in this probability distribution represents the likelihood that the input scalp image 10' or 10" belongs to a particular condition. The output of the positive classifier 142 is a set of predictions (hereinafter referred to as "first set of predictions 142*a*"), each corresponding to a specific scalp condition (in this embodiment: folliculitis, seborrheic dermatitis, oily dandruff, psoriasis, dry dandruff, and normal scalp). Typically, the condition with the highest probability is selected as the final prediction of the positive classifier 142 for the input image. However, the entire probability distribution is retained for subsequent processing stages.

In this embodiment, the negative classifier 144 complements the positive classifier 142 by determining the conditions that the input scalp images 10 and 10' do not represent. The negative classifier 144 aims to enhance the robustness of the scalp condition classification system 100 by explicitly identifying and learning negative examples (i.e., cases where the scalp images 10 and 10' do not belong to certain classes). Similar to the positive classifier 142, the negative classifier 144 in this embodiment may consist of one or more fully connected neural network layers. However, the negative classifier 144 does not generate a probability distribution of scalp conditions that the scalp images 10 and 10' may represent. Instead, it generates a distribution of conditions that the scalp images 10 and 10' are unlikely to represent.

The output of the negative classifier 144 is a set of predictions (hereinafter referred to as "second set of predictions 144*a*") indicating the conditions that the input scalp images 10 and 10' are least likely to correspond to. By processing the same augmented feature vectors as the positive classifier 142, the negative classifier 144 provides a complementary perspective, aiding in refining the overall classification process by eliminating incorrect options. This is particularly useful when the images contain features that may superficially resemble multiple conditions, enabling the scalp condition classification system 100 to more effectively narrow down the range of possibilities.

In this embodiment, the scalp condition classification system 100 integrates the outputs of two classifiers, namely the positive classifier 142 and the negative classifier 144, to generate the final classification decision. This integration involves analyzing the predictions of both classifiers to ensure that the selected scalp condition is not only the most probable according to the scalp condition classification system 100 but also not strongly negated by the negative classifier 144. The decision logic of the scalp condition classification system 100 may include directly comparing the outputs of the positive classifier 142 and the negative classifier 144, or applying additional rules to reconcile any discrepancies between them. For example, the system may prioritize scalp conditions that the positive classifier 142 assigns high confidence levels while simultaneously ensuring that these conditions are not strongly negated by the negative classifier 144, thereby providing the most accurate estimate of the scalp condition.

Figure 4:
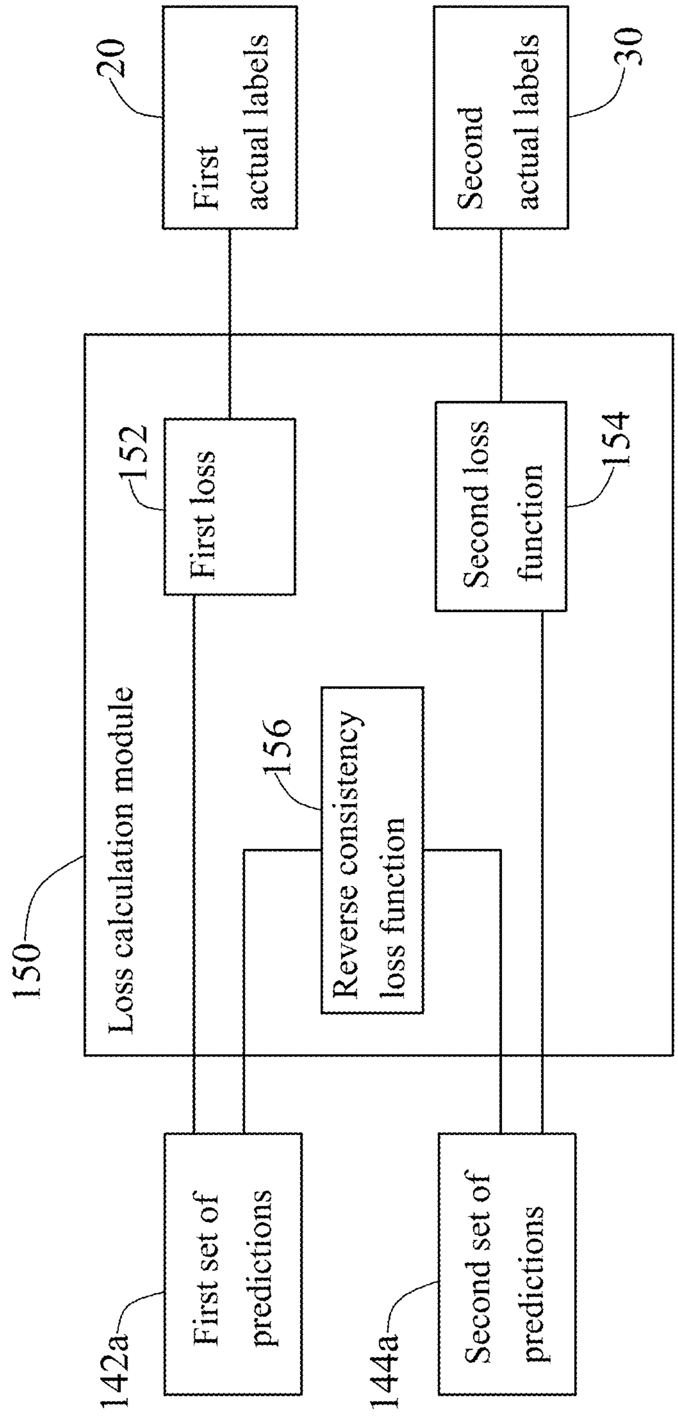
FIG. 4 is a block diagram of an embodiment of the loss calculation module.

Referring to FIG. 1 and FIG. 4, FIG. 4 illustrates a block diagram of an embodiment of the loss calculation module within the scalp condition classification system. The loss calculation module 150 is responsible for overseeing the calculation of losses during the training process. Supervised loss calculation is a critical component of the AI model training process, ensuring that the scalp condition classification system 100 can make accurate predictions based on actual labels.

The loss calculation module 150 includes a first loss function 152, which computes the loss by comparing the first set of predictions 142*a* generated by the positive classifier 142 with the first actual labels 20 annotated by experts. Additionally, the loss calculation module 150 includes a second loss function 154, which computes the loss by comparing the second set of predictions 144*a* generated by the negative classifier 144 with the second actual labels 30 annotated by experts. The scalp condition classification system 100 relies on these first actual labels 20 and second actual labels 30, with each input scalp image corresponding to the correct scalp condition. These first actual labels 20 and second actual labels 30 serve as the standard for evaluating the model's predictions.

In this embodiment, the first loss function 152 and the second loss function 154 of the loss calculation module 150 typically utilize a cross-entropy loss function to compute the supervised losses. The cross-entropy loss function measures the difference between the predicted probability distribution and the actual labels. The cross-entropy loss is defined as follows:

$$L_{sup} = -\sum_{i=1}^{c} y_i \log(p_i)$$

where $y_i$ is the actual label (with $y_i=1$ for the correct class and $y_i=0$ for other classes), and $p_i$ is the predicted probability for a particular class. The cross-entropy loss penalizes incorrect predictions, encouraging the model to adjust its parameters to increase the probability of the correct class.

During the training process, the parameters of the AI model are optimized to minimize the supervised loss across the entire training dataset. This process involves backpropagation and gradient descent, wherein the AI model iteratively updates its weights to reduce the total loss, thereby enhancing its accuracy in predicting scalp conditions.

In addition to the supervised losses calculated by the first loss function 152 and the second loss function 154, the scalp condition classification system 100 also employs a reverse consistency loss function 156 to further refine the AI model's predictions and enhance its robustness. The reverse consistency loss is derived from the outputs of both the positive classifier 142 and the negative classifier 144, encouraging the model to maintain consistent predictions from different perspectives.

The reverse consistency loss ensures that the predictions of the positive classifier 142 (identifying what the scalp image represents) and the negative classifier 144 (identifying what the scalp image does not represent) are logically consistent. For example, if the positive classifier strongly predicts that a scalp image represents a specific condition, the negative classifier should not strongly predict that the same scalp image does not represent that condition.

The reverse consistency loss can be calculated by comparing the outputs of the positive classifier 142 and the negative classifier 144 and penalizing any discrepancies between them. One method to implement the reverse consistency loss function 156 is by using Kullback-Leibler (KL) divergence or Mean Squared Error (MSE) loss functions, which measure the difference between the outputs of the positive classifier 142 and the negative classifier 144:

$$L_{rc} = -\frac{1}{2}\sum_{i=1}^{c}(p_i - (1 - n_i))$$

where $p_i$ is the predicted probability from the positive classifier 142 for class i, and $n_i$ is the predicted probability from the negative classifier 144 for class i. This loss function encourages the AI model to generate consistent predictions between the positive and negative classifiers 142 and 144, thereby improving overall accuracy.

The total loss function used for training the model combines both the supervised loss and the reverse consistency loss, and is defined as follows:

$$L_{total} = L_{sup} + \lambda L_{RC}$$

where λ is a weighting factor used to balance the contribution of the reverse consistency loss. By optimizing the total loss function, the AI model is trained to produce accurate, consistent, and well-calibrated predictions. The training process involves iteratively optimizing the AI model's parameters to minimize the total loss function. This process occurs over multiple training epochs, during which the AI model is exposed to the entire training dataset, progressively refining its predictions. In this embodiment, the training dataset consists of a diverse set of scalp images, each annotated with the correct scalp condition. The training dataset may include scalp images captured under various conditions (e.g., different lighting, resolutions) to ensure that the AI model generalizes well across different scenarios. In each training iteration, the AI model's predictions are compared with the actual labels, and the total loss is calculated. The loss gradients are then backpropagated through the neural network, allowing the AI model to update its weights using optimization algorithms such as Stochastic Gradient Descent or Adam. The training process continues until the AI model's performance converges, meaning that further training yields only minimal improvements in accuracy.

By minimizing the total loss function, which includes both supervised loss and reverse consistency loss, the training process ensures that the AI model not only makes accurate predictions but also maintains logical consistency and confidence in its predictions. This comprehensive approach results in a more robust and reliable scalp condition classification system 100, capable of performing effectively under diverse imaging conditions and challenging scenarios.

Referring again to FIG. 1, the adaptive update module 160 is responsible for ensuring that the scalp condition classification system 100 maintains accurate and reliable classification performance during inference, even when faced with variability in scalp image conditions. The adaptive update module 160 employs a sharpness-aware and reliable entropy minimization strategy to adjust the AI model in real-time, addressing challenges arising from differences in imaging devices 105, environmental factors, and other external variables.

The adaptive update module 160 utilizes a sharpness-aware entropy minimization technique, guiding the AI model to converge toward flat minima in the loss landscape. Flat minima refer to regions in the model parameter space where small perturbations to the input data or model parameters do not significantly affect the loss value. By converging to these flat minima, the AI model becomes more robust to variations in test data, reducing the likelihood of misclassifications due to minor changes in image quality or presentation.

In addition to sharpness-aware optimization, the adaptive update module 160 implements a reliable entropy-based adaptation mechanism. This includes minimizing the entropy of the AI model's predictions for scalp images, thereby increasing the confidence of its predictions. However, to prevent overconfidence in erroneous predictions, the adaptive update module 160 introduces a filtering mechanism that identifies and excludes noisy samples that generate large gradient norms during the entropy minimization process. This filtering step ensures that only reliable data contribute to the AI model's adaptation, enhancing the stability of the inference process.

Medical image classification, including scalp condition classification, faces significant challenges due to variability in imaging conditions such as lighting, resolution, and differences in imaging devices. The adaptive update module 160 is specifically designed to address these challenges, ensuring that the AI model performs consistently well across a wide range of conditions.

The scalp condition classification system 100 may encounter test images captured by different types of imaging devices, each with its unique characteristics. Additionally, images may be taken under varying environmental conditions, such as different lighting levels or angles. These factors can introduce substantial variability into the test data, potentially impacting the model's performance if not properly managed. To address this variability, the adaptive update module 160 performs real-time adaptation during the inference process. As each test image is processed, the adaptive update module 160 dynamically adjusts the AI model's parameters based on the current data, ensuring that the AI model aligns with the specific features of the input image. This adaptation process is guided by the sharpness-aware and reliable entropy minimization strategies, ensuring that the model maintains stability and confidence in its predictions.

The filtering mechanism of the adaptive update module 160 plays a crucial role in maintaining the quality of the adaptation process. By identifying and excluding samples that produce large gradient norms during entropy minimization, the adaptive update module 160 prevents noisy or anomalous data from disrupting the model's stability. This approach enhances the system's ability to maintain high performance, even when confronted with challenging or atypical test images.

Figure 5:
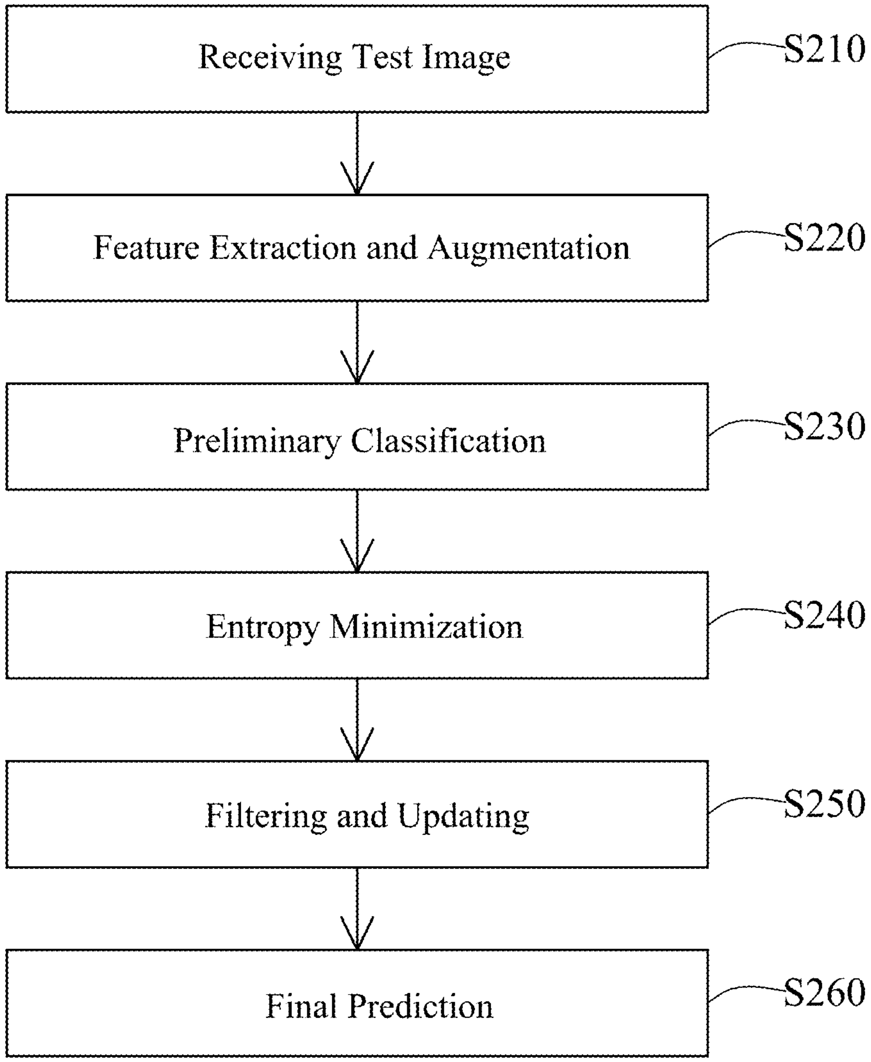
FIG. 5 is a flowchart illustrating the operation of the adaptive update module during the inference process of the present embodiment.

Referring to FIG. 5, which illustrates a flowchart of the operation of the adaptive update module 160 during the inference process, the adaptive update module 160 operates as follows:

Step S210 (Receiving Test Image): The scalp condition classification system 100 receives a test scalp image, which may have been captured under different conditions compared to the training images (e.g., scalp image 10 in FIG. 3A).

Step S220 (Feature Extraction and Augmentation): The test scalp image is processed by the encoder 120 and the prototype-based augmentation module 130, generating augmented feature vectors.

Step S230 (Preliminary Classification): The positive classifier 142 generates preliminary predictions (i.e., the first set of predictions 142*a*) based on the augmented feature vectors.

Step S240 (Entropy Minimization): The adaptive update module 160 calculates the entropy of the preliminary predictions and applies the sharpness-aware entropy minimization strategy to adjust the AI model's parameters, guiding the AI model toward convergence at flat minima in the loss landscape.

Step S250 (Filtering and Updating): The adaptive update module 160 filters out noisy samples by identifying and excluding those that generate large gradient norms during the entropy minimization process. This ensures that only reliable data contribute to the adaptation, and the AI model's parameters are updated accordingly.

Step S260 (Final Prediction): After adaptation, the scalp condition classification system 100 generates the final classification decision for the test scalp image, reflecting the most probable scalp condition based on the current data.

This adaptive inference process enables the scalp condition classification system 100 to maintain consistent and accurate performance across diverse imaging conditions, making it a powerful tool for diagnosing scalp conditions.

The present invention can be implemented in various forms beyond the primary embodiments described above. The following additional embodiments provide alternative methods that can be adjusted according to specific needs or constraints in different clinical environments.

Although the primary embodiments utilize rotation and swapping techniques for image augmentation, other methods may also be employed to preserve the integrity of the original image features. For example, the scalp image 10" in FIG. 3A may be augmented using contrast adjustment. This technique involves altering the contrast levels of the image to simulate different lighting conditions without removing any part of the scalp image. This helps the AI model generalize across images captured under varying lighting environments. Additionally, slight variations in the hue, saturation, and brightness of the scalp image can be applied. This is particularly useful for scalp images where scalp or hair color may vary due to different lighting conditions or imaging devices.

The following hypothetical examples illustrate how the present invention can be applied in real-world scenarios.

Example 1: Classification of Folliculitis

A patient presents with suspected folliculitis of the scalp. The scalp condition classification system 100 receives an image of the patient's scalp, which is processed by the image preprocessing module 110 to generate augmented versions. The encoder 120 extracts features from these images, and the prototype-based augmentation module 130 refines these features using prototypes related to folliculitis and other similar conditions. The positive classifier 142 predicts folliculitis as the most probable condition, while the negative classifier 144 excludes other possibilities, such as seborrheic dermatitis. The final classification confirms the presence of folliculitis, enabling healthcare professionals to provide appropriate treatment or care for the patient.

Example 2: Handling Image Variability

A series of scalp images are captured under different lighting conditions and using various imaging devices. During testing or inference, the scalp condition classification system 100 processes each image through the adaptive update module 160. Despite variations in image quality and appearance, the scalp condition classification system 100 successfully adapts to each scenario, minimizing entropy loss through the sharpness-aware strategy and filtering out noisy samples. The final classifications remain consistent across different conditions, demonstrating the system's robustness in the face of image variability.

Example 3: Real-World Clinical Application

In a busy dermatology clinic, the scalp condition classification system 100 is integrated into the workflow to assist in diagnosing scalp conditions. As each patient's scalp image is captured, the scalp condition classification system 100 quickly processes the image and provides reliable and accurate classifications in real-time. Dermatologists use these classifications as a second opinion, cross-referencing them with their own assessments. The ability of the scalp condition classification system 100 to handle a wide range of conditions and adapt to different imaging scenarios makes it a valuable tool for improving diagnostic accuracy and efficiency within the clinic.

Advantages Over Existing Scalp Condition Classification Methods

Compared to existing scalp condition classification methods, the present invention offers several significant advantages:

1. Enhanced Accuracy: By utilizing a prototype-based augmentation module and a dual-classifier approach, the scalp condition classification system achieves higher classification accuracy than traditional methods. The use of prototypes ensures that the AI model leverages prior knowledge about scalp conditions, while the positive and negative classifiers provide a comprehensive assessment of the input images.

2. Robustness to Environmental Variability: The adaptive update module allows the system to maintain stable performance under varying imaging conditions, such as changes in lighting, resolution, and device differences. The sharpness-aware and reliable entropy minimization strategies ensure that the model remains resilient to variations in test data, reducing the likelihood of misclassifications.

3. Retention of Diagnostic Features: The image preprocessing module is specifically designed to preserve all relevant features in the input images, avoiding common issues associated with traditional augmentation techniques like cropping. This ensures that no potential symptoms are lost during processing, which is crucial for accurate diagnosis.

In summary, the present invention not only enhances the diagnostic process by providing automated and accurate scalp condition classification but also offers a flexible and scalable solution that can be integrated into various clinical workflows. The combination of advanced feature extraction, prototype-based augmentation, and adaptive inference ensures that the scalp condition classification system 100 can effectively handle the complexities of scalp image classification.

What is claimed is:

1. A scalp condition classification system comprising:

an image preprocessing module configured to receive an input scalp image and generate multiple augmented images by applying operations that preserve all original features of the scalp image;

an encoder configured to extract features from the augmented images;

a prototype-based augmentation module configured to augment the extracted features by combining multiple prototype features corresponding to predefined scalp conditions to form augmented features;

a classification module comprising:

a positive classifier configured to process the augmented features and output a first set of predictions; and a negative classifier configured to process the augmented features and output a second set of predictions; and a loss calculation module configured to calculate a supervised loss using multiple actual labels and to calculate a reverse consistency loss between the first set of predictions and the second set of predictions.

2. The scalp condition classification system of claim 1, wherein the prototype-based augmentation module is further configured to select the prototype features based on a similarity measure between the extracted features and a set of predefined class prototypes.

3. The scalp condition classification system of claim 2, wherein the similarity measure is calculated using cosine similarity, and the prototype features are integrated into the extracted features using a temperature-scaled softmax function.

4. The scalp condition classification system of claim 1, wherein the augmented images are generated by applying operations that include rotating the scalp image by predetermined angles and swapping portions of the scalp image, while ensuring the preservation of all original features of the scalp image to avoid the removal of any potential symptoms.

5. The scalp condition classification system of claim 1, wherein the supervised loss is calculated using multiple first actual labels corresponding to the first set of predictions, and the reverse consistency loss is calculated using multiple second actual labels corresponding to the second set of predictions.

6. The scalp condition classification system of claim 1, further comprising an adaptive update module configured to update the scalp condition classification system during an inference process by minimizing a sharpness-aware and reliable entropy loss to ensure stable classification performance across different imaging devices and environments.

7. The scalp condition classification system of claim 6, wherein the adaptive update module is further configured to adjust the scalp condition classification system by identifying and filtering out samples that generate large gradient norms during the entropy minimization process.

8. The scalp condition classification system of claim 6, wherein the adaptive update module further ensures that the system converges to flat minima in loss calculations during the inference process, thereby enhancing robustness to noisy updates.

9. The scalp condition classification system of claim 1, wherein the prototype-based augmentation module is configured to update the prototype features based on newly received scalp images during the training process.

10. The scalp condition classification system of claim 1, further comprising a memory bank configured to store the extracted features and corresponding actual labels during the training process, wherein the prototype-based augmentation module is further configured to update the prototypes using the features stored in the memory bank.

11. The scalp condition classification system of claim 1, wherein the augmented images are generated by applying operations that avoid cropping methods, thereby preserving the integrity of the original medical images.

12. A method for classifying scalp conditions using an Artificial Intelligence (AI) model, the method comprising:

receiving an input scalp image;

generating multiple augmented images by applying operations that preserve all original features of the scalp image;

extracting features from the augmented images using an encoder of the AI model;

enhancing the extracted features by combining multiple prototype features corresponding to predefined scalp conditions using a prototype-based augmentation module to form augmented features;

processing the augmented features through a positive classifier of the AI model to output a first set of predictions;

processing the augmented features through a negative classifier of the AI model to output a second set of predictions; and calculating a supervised loss using multiple actual labels and calculating a reverse consistency loss between the first set of predictions and the second set of predictions.

13. The method of claim 12, wherein the step of enhancing the extracted features further comprises selecting prototype features based on a similarity measure between the extracted features and a set of predefined class prototypes.

14. The method of claim 13, wherein the similarity measure is calculated using cosine similarity, and the prototype features are integrated into the extracted features using a temperature-scaled softmax function.

15. The method of claim 12, wherein the step of generating multiple augmented images comprises applying operations that include rotating the scalp image by predetermined angles and swapping portions of the scalp image, while ensuring the preservation of all original features of the scalp image to avoid the removal of any potential symptoms.

16. The method of claim 12, further comprising adjusting the AI model during an inference process by minimizing a sharpness-aware and reliable entropy loss to ensure stable classification performance across different imaging devices and environments.

17. The method of claim 16, further comprising adjusting the AI model by identifying and filtering out samples that generate large gradient norms during the entropy minimization process.

18. The method of claim 16, further comprising ensuring that the AI model converges to flat minima in loss calculations during the inference process, thereby enhancing robustness to noisy updates.

19. The method of claim 12, further comprising updating the prototype features based on newly received scalp images during the training process.

* * * * *